United States Patent [19]

Eichhorn et al.

[11] Patent Number: 4,740,644
[45] Date of Patent: Apr. 26, 1988

[54] PREPARATION OF 1,2-DICHLOROETHANE BY OXYCHLORINATION OF ETHYLENE OVER A COPPER-CONTAINING SUPPORTED CATALYST

[75] Inventors: Hans-Dieter Eichhorn, Ludwigshafen; Hans H. Schneehage, Weisenheim, both of Fed. Rep. of Germany; Luc Cordemans, Kapellen, Belgium; Werner Hebgen, Nussloch, Fed. Rep. of Germany; Christof Jaeckh, Heidelberg, Fed. Rep. of Germany; Wolf D. Mross, Frankenthal, Fed. Rep. of Germany

[73] Assignee: BASF Aktiengesellschaft, Ludwigshafen, Fed. Rep. of Germany

[21] Appl. No.: 876,760

[22] Filed: Jun. 20, 1986

[30] Foreign Application Priority Data

Jun. 22, 1985 [DE] Fed. Rep. of Germany ....... 3522474

[51] Int. Cl.$^4$ .................. C07C 17/2; C07C 17/156
[52] U.S. Cl. ................................. 570/245; 570/243; 502/225
[58] Field of Search ................ 570/245, 243; 502/225

[56] References Cited

U.S. PATENT DOCUMENTS

| 3,184,515 | 2/1962 | Penner et al. | 260/658 |
| 3,892,816 | 7/1975 | Kester | 570/245 |
| 4,206,180 | 6/1980 | Campbell et al. | 570/245 |

FOREIGN PATENT DOCUMENTS

| 2356549 | 10/1975 | Fed. Rep. of Germany | 570/245 |
| 2651974 | 5/1978 | Fed. Rep. of Germany | . |
| 3130552 | 2/1983 | Fed. Rep. of Germany | . |
| 1104666 | 2/1968 | United Kingdom | . |

*Primary Examiner*—J. E. Evans
*Attorney, Agent, or Firm*—Keil & Weinkauf

[57] ABSTRACT

1,2-Dichloroethane is prepared by oxychlorination of ethylene in the presence of a catalyst which contains, on a conventional carrier, copper(II) chloride in a concentration such that the amount of copper ions is from 1 to 20% by weight, based on the total weight of the catalyst, by a process in which the catalyst is obtained by impregnating the carrier with an aqueous solution which contains copper(II) chloride and hydrogen chloride in amounts such that the weight ratio of copper ions to hydrogen chloride is from 13:1 to 130:1.

8 Claims, No Drawings

PREPARATION OF 1,2-DICHLOROETHANE BY OXYCHLORINATION OF ETHYLENE OVER A COPPER-CONTAINING SUPPORTED CATALYST

The present invention relates to a process for the preparation of 1,2-dichloroethane by oxychlorination of ethylene over a supported catalyst containing copper and alkali metals. It furthermore relates to the catalyst used for this purpose.

The oxychlorination of ethylene by reaction with hydrogen chloride and oxygen is a known process carried out industrially on a large scale. The catalyst used in such a process contains copper(II) chloride or copper oxychloride on a porous, refractory carrier, such as activated alumina, silica, an aluminosilicate or kieselguhr. The catalyst may furthermore contain additives, such as alkali metal chlorides, metal chlorides or rare earths and other metal compounds which activate the desired reaction and/or prevent undesirable side reactions.

In carrying out this process, the required oxygen, if appropriate in the form of air, is passed together with HCl and ethylene over a single catalyst layer which is operated under highly isothermal conditions by removing heat in a suitable manner (cf. U.S. Pat. No. 3,184,515). According to GB-A-1 104 666, the reaction of ethylene with hydrogen chloride and air or oxygen can also be carried out in a plurality of reactors arranged in series. In this procedure, both air or oxygen and hydrogen chloride can be divided into a plurality of streams and fed separately to each reactor.

In another version of this process, some of the reaction mixture emerging from the reaction zone is mixed with fresh ethylene, hydrogen chloride and air or oxygen, and recycled to the reaction zone. If necessary, some or all of the 1,2-dichloroethane and water can be separated off from the reaction mixture prior to recycling (cf. DE-A-3 130 552).

When carrying out an oxychlorination process, it is particularly important to control the temperature in the catalyst layer. Since the oxychlorination reaction is highly exothermic, there is a danger that undesirably high, localized temperature zones (hot spots) may form in the catalyst layer. These may lead to destruction of the catalyst, with the result that the latter disintegrates and the pressure loss above the catalyst bed increases. This leads to a loss of efficiency of the oxychlorination plant, so that the catalyst has to be replaced or regenerated at high costs. Furthermore, hot spots in the catalyst layer lead to a substantial number of undesirable side reactions, reducing the yields of 1,2-dichloroethane.

Many measures have been suggested for preventing or at least reducing such hot spots. For example, DE-B2 356 549 proposes controlling the temperature by diluting the starting materials with an inert gas, by varying the ratios of the starting materials, by diluting the catalyst particles with inert material or by varying the particle size of the catalyst and/or of the inert particles.

Inert material suggested for diluting the catalysts was silica, alumina, graphite, glass and ceramic particles in a very wide variety of forms, such as pellets, spheres, rings or extrudates. The ratio of catalyst to inert material in the reactor can be varied and adapted to the requirements of the reaction. Advantageously, the highest concentration of inert material is present at the entrance of the reactor, and the concentration then decreases gradually or stepwise towards the reactor outlet. Hence, a plurality of zones having different ratios of catalyst to inert material may be present in the reactor.

It is also possible to use catalysts having a reduced activity. This makes it possible to create zones of low activity in the reactor in regions where high temperature peaks occur, the said zones effectively reducing such hot spots. In a single-stage oxychlorination process, the activity of the catalyst in this case increases from the reactor entrance to the reactor exit, whereas in a multi-stage procedure the activity may increase from stage to stage. Furthermore, the individual catalysts may also be mixed with inert material (cf. GB-A-1 104 666).

Various measures have been proposed for the preparation of catalysts of different activities. One possible method for controlling the activity comprises varying the concentrations of copper(II) chloride, which is usually present in amounts corresponding to 1–20% by weight, based on the total catalyst material, of copper. Catalysts of low activity therefore generally have lower copper concentrations than those of high activity, so that, according to the proposal in GB-A-1 104 666, the concentration of copper compound on the carrier is increased in the direction of product flow.

In another possible method for reducing the activity of the catalyst, the latter is doped with alkali metal salts, preferably in the form of their chlorides, eg. potassium chloride, sodium chloride, lithium chloride and other alkali metal chlorides. Up to 3% by weight of alkali metals may be present in the catalyst; according to DE-A-3 130 552, the activity is generally too low at higher concentrations. According to the said publication, catalysts of low activity can also be prepared by combining both possible methods, ie. lower copper concentrations and doping with alkali metals.

While catalyst zones of low activity are thus most advantageously used at the reactor entrance, the activity of the catalyst must increase in the direction of product flow and must be highest at the reactor exit, where, because of the low partial pressures of the reactants, the danger of temperature peaks is very small, so that very high conversion of the starting materials is ensured.

Suitable carriers for the catalyst, the amount of which makes the overall amount of catalyst up to 100%, are principally alumina, silica, mixtures of alumina and silica, and aluminosilicates. $\gamma$-Alumina which has a BET specific surface area from 80 to 350 m$^2$/g and a pore volume of from 0.4 to 1.0 cm$^3$/g is preferably used. Regarding the activity, the carrier form chosen also plays a certain role. Suitable forms of the carrier are pellets, spheres or rings (cf. DE-B-2 356 549).

The catalyst is prepared by impregnating the carrier once or several times with a solution containing the active components and the promoters. This is followed by drying at from 100° to 500° C. in air, an inert gas, e.g. nitrogen, or a mixture of the two. Various methods have been proposed for applying the active components:

In the method described in GB-A-1 104 666, the carrier is impregnated with aqueous solutions of copper(II) chloride and, if required, alkali metal salts and other promoters, e.g. chlorides of the rare earth metals, and then dried. DE-B-2 356 549 proposes impregnating the carrier with an aqueous solution which, in addition to alkali metal ions, contains copper(II) oxychloride and hydrogen chloride in amounts such that the weight ratio of copper ions to hydrogen chloride is from 2:1 to 1:1. This is followed by treatment at up to 300° C., significant amounts of oxygen being excluded.

The oxychlorination process itself, in the form of a single-stage or multi-stage procedure, with or without gas recycling, is familiar to the skilled worker. The temperatures in the reactors should in general be from 200° to 320° C., and the pressures from 2 to 10 bar.

The disadvantage of the catalysts used in the conventional oxychlorination processes is the fact that, in spite of all the measures mentioned, disintegration of the catalyst takes place over a period of time, resulting in an increase in pressure loss above the catalyst bed, so that the catalyst has to be replaced. Moreover, these catalysts give incomplete conversions of the starting materials, which indicates that the catalysts, which should have a high activity at low partial pressures of the reactants, still possess insufficient activity. Furthermore, certain amounts of undesirable by-products are formed, especially ethyl chloride, which reduces the yields of 1,2-dichloroethane and has to be converted back to non-hazardous substances by expensive measures after 1,2-dichloroethane has been isolated.

It is an object of the present invention to provide a process for the preparation of 1,2-dichloroethane by oxychlorination of ethylene, and an oxychlorination catalyst which permits the preparation of 1,2-dichloroethane over a long period with high efficiency, high yield and the production of only small amounts of by-products.

We have found that this object is achieved by a process of the stated type, which is carried out in the presence of a catalyst which contains, on a conventional carrier, copper(II) chloride in a concentration corresponding to 1-20% by weight, based on the total weight of the catalyst, of copper ions. In the process, the catalyst is obtained by impregnating the carrier with an aqueous solution which contains copper(II) chloride and hydrogen chloride in amounts such that the weight ratio of copper ions to hydrogen chloride is from 13:1 to 130:1.

Subclaims 2 to 5 relate to preferred embodiments of the novel process. The catalyst according to the invention has the features described in claim 6, and preferably also those described in claims 7 and 8.

The impregnating solution is prepared by dissolving copper(II) chloride, which has the chemical formula $CuCl_2 \cdot 2H_2O$, and, if desired, potassium chloride and other promoters in water, and adding hydrogen chloride, preferably in the form of an aqueous solution, so that the weight ratio of copper ions to hydrogen chloride in the impregnating solution is from 13:1 to 130:1, preferably from 25:1 to 50:1. The sequence in which the individual components are dissolved is not critical. What is important is that the impregnating solution contains copper ions and hydrogen chloride in the ratio according to the invention.

If the impregnating solution contains an excessively large amount of hydrogen chloride, for example a ratio of copper ions to hydrogen chloride of from 2:1 to 1:1, as in the prior art (DE-B-2 356 549), when the oxychlorination process is carried out substantially lower lives and lower conversions and yields are obtained than when the novel catalysts are used.

If, on the other hand, the oxychlorination process is carried out using an impregnating solution without any added hydrogen chloride, as in the prior art (GB-A-1 104 666), substantially lower conversions and yields, coupled with lower lives, are achieved compared with the use of the novel catalysts.

Suitable carriers for this catalyst system are the conventional ones. $\gamma$-$Al_2O_3$ having a BET surface area of from 100 to 250 $m^2/g$ is preferably used. Suitable shapes for the carriers are the conventional geometric shapes, rings, tablets and spheres being particularly preferred.

The concentration of copper(II) chloride on the catalyst corresponds to 1-20, preferably 2-13, in particular 3-9, % by weight of copper. The concentration itself must be adjusted according to the desired activity of the catalyst and the requirements of the reaction. Alkali metal salts, preferably the chlorides, and chlorides of the rare earths may additionally be applied onto the carrier, as promoters. Potassium chloride is a particularly preferred promoter and is applied in a molar ratio of copper to potassium of from 1:1 to 10:1. In order to apply the desired amount of active component and promoter, the catalyst can be impregnated once or several times. It is not absolutely necessary for the active component and the promoters to be applied simultaneously onto the carrier. It is possible, for example, for copper(II) chloride and hydrogen chloride to be applied first and then the promoters, or vice versa. When the carrier is impregnated with the solution, the total amount of liquid should correspond roughly to the water absorption capacity of the carrier. The technique of impregnation and drying of the carrier is familiar to the skilled worker and is described in, for example, DE-B-2 356 549. Drying of the impregnated catalyst should be carried out at from 100° to 500° C., preferably up to 300° C., advantageously under nitrogen. However, a small amount, ie. up to about 3%, of oxygen can be accepted and is not disadvantageous.

The oxychlorination process using the novel catalyst system may be carried out as a single-stage or multi-stage process. In the multi-stage procedure, it is also possible for individual starting materials, e.g. air or oxygen or hydrogen chloride, to be fed separately to individual stages.

In the single-stage or multi-stage procedure, some of the reaction mixture emerging from the reaction zone can also be mixed with fresh ethylene, hydrogen chloride and air or oxygen and then recycled to the reaction zone. If necessary, some or all of the dichloroethane and water can be isolated from the reaction mixture prior to recycling. The temperatures in the catalyst beds should be at the usual values of from 200° to 320° C., and the pressures should be up to about 10 bar.

To avoid excessive temperature peaks in the catalyst bed, it may be advantageous, when the process is carried out using the novel catalyst system, to change the activity of the catalyst in steps, so that it increases in the direction of product flow in the reactor in the case of a single-stage procedure, or in the direction of product flow in one or more stages in the case of a multistage procedure. The catalyst's activity can be changed stepwise by known measures, for example by changing the copper(II) chloride concentration of the catalyst, by doping the catalyst with alkali or by adding diluents.

The Examples which follow illustrate the invention.

EXAMPLE 1

Preparation of a novel catalyst 1,000 g of annular $\gamma$-alumina pellets having a height of 5 mm, an external diameter of 5 mm and a wall thickness of 1.6 mm are impregnated. The water absorption of the carrier is 0.48 cm³/g. The carrier is impregnated with 880 cm³ of an aqueous solution which contains 319.8 g of CuCl₂.2H₂O, 24.2 g of KCl and 11.2 g of concentrated hydrochloric acid (37% strength). Thereafter, drying is carried out under nitrogen for 17 hours at 70° C., for 3 hours at 120° C. and then for 3 hours at 210° C.

COMPARATIVE EXAMPLE 1

Preparation of a prior art catalyst (a) 1,000 g of annular γ-Al₂O₃ pellets are impregnated with 880 cm³ of an aqueous solution which contains 319.8 g of CuCl₂.2H₂O and 24.2 g of KCl. Impregnation and drying are carried out by the method described in Example 1.

(b) 1,000 g of annular γ-Al₂O₃ pellets are impregnated with 880 cm³ of in aqueous solution which contains copper oxychloride and hydrogen chloride in amounts such that the weight ratio of copper ions to hydrogen chloride is 1:1. The impregnating solution also contains 24.2 g of KCl. The relative amounts of copper and potassium per carrier unit, and the impregnating and drying procedures are similar to Example 1 and Comparative Example 1a).

EXAMPLE 2

Testing the catalysts (a) Activity and selectivity tests 90 cm³ of catalyst are introduced into a stainless steel tube having an internal diameter of 64 mm, and a gas mixture containing 0.986 mole/hour of hydrogen chloride, 0.493 mole/hour of ethylene and 0.246 mole/hour of oxygen is passed through the catalyst, the oxygen being introduced in the form of air. Some of the gas emerging from the catalyst bed is mixed with fresh starting gas and recycled to the reaction zone. The ratio of recycled reaction gas to fresh starting gas is 20:1. The temperature in the catalyst bed is 200° C. and the pressure is 1 bar. When a steady operating state has been reached, samples of the gas emerging from the reaction zone are taken and are used to determine the conversion and the yield of 1,2-dichloroethane. The percentage of hydrogen chloride converted is stated as a measure of the conversion, while the selectivity in the form of the percentage of reacted ethylene which is converted to 1,2-dichloroethane, to ethyl chloride and to other products is stated as a measure of the yield.

(b) Test of catalyst life

To test the life of the catalyst, 25 g of catalyst are introduced into a stainless steel reactor having an internal diameter of 10 mm. The pressure loss in the catalyst bed is measured at room temperature while passing through 600 l/hour of nitrogen and under a pressure of 1.5 m (water column) upstream of the bed. The reactor is then heated to 250° C. with a molten salt, and a gas containing 16.9 l/hour of hydrogen chloride, 15.9 l/hour of ethylene and 32.9 l/hour of air is passed through the catalyst. After 6 days, the reactor is cooled under nitrogen, and the pressure loss under the above conditions is measured again. The catalyst is then removed, and the amount of catalyst which has disintegrated into particles smaller than 1 mm is determined.

The percentage increase in the pressure loss and the percentage of fine particles in the catalyst removed are stated as a measure of the life of the catalyst.

The results of the experiments are summarized on the Table below.

TABLE

| | According to the invention | Prior art according to Comparative Example 1 | |
|---|---|---|---|
| | | (a) | (b) |
| HCl conversion in % | 29.2 | 22.4 | 27.8 |
| Amount of ethylene, in mol %, converted to 1,2-Dichloroethane | 99.84 | 99.62 | 99.42 |
| Ethyl chloride | 0.14 | 0.26 | 0.50 |
| Remainder | 0.02 | 0.12 | 0.08 |
| Increase in pressure loss, in % | 27 | 42 | 135 |
| Fine fractions smaller than 1 mm, % by weight | 7.5 | 7.7 | 11.2 |

The results show that when the oxychlorination process is carried out using the novel catalysts better results are obtained than when catalysts prepared according to the prior art were used.

Both the activity and the yield of 1,2-dichloroethane are higher when the catalysts according to the invention are used, while smaller amounts of by-products are obtained. In particular, the catalyst life is also longer when the novel catalyst is used; this is evident from the smaller increase in the pressure loss of the catalyst bed and from the smaller amount of fine particles.

We claim:

1. A process for the preparation of 1,2-dichloroethane by oxychlorination of ethylene in the presence of a catalyst which contains, on a conventional carrier, copper(II) chloride in a concentration corresponding to 1–20% by weight, based on the total weight of the catalyst, of copper ions, wherein the catalyst is obtained by impregnating the carrier with an aqueous solution which contains copper(II) chloride and hydrogen chloride in amounts such that the weight ratio of copper ions to hydrogen chloride is from 13:1 to 130:1.

2. The process of claim 1, wherein the aqueous solution contains copper(II) chloride and hydrogen chloride in amounts such that the weight ratio of copper ions to hydrogen chloride is from 25:1 to 50:1.

3. The process of claim 1, wherein the aqueous solution additionally contains potassium chloride in an amount such that the weight ratio of copper ions to potassium ions is from 1:1 to 10.1.

4. The process of claim 1, wherein the copper(II) chloride is present on the carrier in a concentration such that the amount of copper ions is from 2 to 13% by weight, based on the total weight of the catalyst.

5. The process of claim 1, wherein the oxychlorination is carried out in two or more reactors arranged in series.

6. The process of claim 5, wherein exit gas which emerges from the reaction zone is completely or partly freed from dichloroethane and water and recycled.

7. The process of claim 5, wherein one or more reactors are divided into different reaction zones.

8. The process of claim 7, wherein the concentrations of copper on the carrier differ in the various reaction zones and increase in the direction of product flow.

* * * * *